US006258963B1

(12) United States Patent
Koch et al.

(10) Patent No.: US 6,258,963 B1
(45) Date of Patent: *Jul. 10, 2001

(54) BENZYLIDENE-γ-BUTYROLACTONES, PROCESS FOR THEIR PREPARATION AND THEIR USE AS UV ABSORBER

(75) Inventors: Oskar Koch, Göttingen; William Johncock, Höxter; Roland Langner, Bevern, all of (DE)

(73) Assignee: Haarmann & Reimer GmbH, Holzminden (DE)

( * ) Notice: This patent issued on a continued prosecution application filed under 37 CFR 1.53(d), and is subject to the twenty year patent term provisions of 35 U.S.C. 154(a)(2).

Subject to any disclaimer, the term of this patent is extended or adjusted under 35 U.S.C. 154(b) by 0 days.

(21) Appl. No.: 09/458,135

(22) Filed: Dec. 9, 1999

(30) Foreign Application Priority Data

Dec. 11, 1998 (DE) ............................................. 198 57 252

(51) Int. Cl.$^7$ .................................................. C07D 307/33
(52) U.S. Cl. ............................ 549/295; 549/323; 424/59; 424/60
(58) Field of Search ..................................... 549/295, 323; 424/59, 60

(56) References Cited

U.S. PATENT DOCUMENTS

| 5,217,709 | 6/1993 | Lagrange et al. | 424/47 |
| 5,961,960 | 10/1999 | Dilk et al. | 424/59 |
| 5,965,066 | 10/1999 | Koch et al. | 252/589 |

FOREIGN PATENT DOCUMENTS

| 0 044 970 | 6/1983 | (EP) . |
| 2222829 | 3/1990 | (GB) . |

OTHER PUBLICATIONS

P. Rioult, J. Vialle: "Composés Organiques Sulfurés XIV. Condensation Des Lactones, Thiolactones et Thiolannethiones–2 Avec Les Aldéhydes Aromatiques et le Sulfure de Carbone", Bull. Soc. Chim. FR., Nr. 11, 1968, Seiten 4477–4483, XP000882402.

H. Zimmer et al: "Substituted Gama–Lactones, IV, Some Aldehyde Condensations with Delta (Beta, Gamma)–Angelica– and Gamma–Valerolactone", J. Org. Chem, Bd 25, 1960, Seiten 838–839, XP000882308.

H. Zimmer et al, "Substituted Gamma–Lactones, XIII, Nitration of Substituted Alpha–Benzylidene–Gamma–Butyrolactones", J. Org. Chem., Bd 29, 1964, Seiten 952–929, XP000882311.

Datta et al, Tetrahedron 43(22), pp. 5367–5374, 1987.*
Torabi et al, J. Org. Chem., 34(12), pp. 3792–3796, 1969.*
Zimmer et al, J. Org. Chem., 25, pp. 838–389, 1960.*
Matsuo et al, Chem. Pharm. Bull, 37(10), pp. 2803–2806, 1989.*

* cited by examiner

Primary Examiner—Ba K. Trinh
(74) Attorney, Agent, or Firm—Joseph C. Gil; Noland J. Cheung

(57) ABSTRACT

The invention relates to modified benzylidene-γ-butyrolactones, to a process for their preparation and to the use as UV absorber, for example in pharmaceutical and cosmetic compositions, sunscreens, daycare and haircare products, for improving industrial products, such as paints, surface coatings, plastics, textiles, packaging materials and rubbers.

21 Claims, No Drawings

BENZYLIDENE-γ-BUTYROLACTONES, PROCESS FOR THEIR PREPARATION AND THEIR USE AS UV ABSORBER

FIELD OF THE INVENTION

The invention relates to modified benzylidene-γ-butyrolactones, to a process for their preparation and to the use as UV absorber, for example in pharmaceutical and cosmetic compositions, sunscreens, daycare and haircare products, for improving industrial products, such as paints, surface coatings, plastics, textiles, packaging materials and rubbers.

BACKGROUND OF THE INVENTION

Depending on their wavelength, UV rays are divided in UV-A rays (320–400 nm) and UV-B rays (280–320 nm). The harmful effect, in particular the occurrence of sunburn (erythema), increases not only with the duration of exposure but also with decreasing wavelength and is thus significantly more strongly marked in the case of UV-B radiation than in the case of UV-A radiation. Since erythemas can occur even after short exposure to the sun, in some cases after 20–30 minutes, efficient protection against this radiation is of particular importance.

For this area of UV protection, a number of UV-B absorbers are already known from the prior art. Examples mentioned are camphor derivatives, salicylic acid derivatives, benzophenones, cinnamates, benzimidazoles and triazines. One example of benzylidene-γ-butyrolactones is described in European Patent Application EP-A 44970. These are compounds of the formula

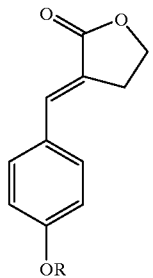

in which

R is a $C_1$–$C_{15}$-alkyl radical, branched or unbranched, phenyl or benzyl.

However, all of these compounds have the disadvantages that they are either in the form of a solid and thus have only limited solubility in the cosmetic preparations, exhibit only low absorption or have photostability which does not meet the necessary criteria and are thus unsatisfactory.

SUMMARY OF THE INVENTION

Accordingly, the object of the present invention is to provide improved UV-B absorbers. This object is achieved by benzylidene-γ-butyrolactones of the general formula

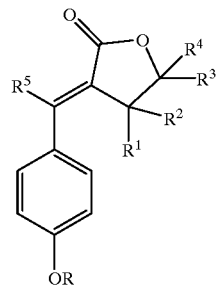

wherein

R is hydrogen or $C_1$–$C_6$-alkyl or cycloalkyl, and $R^1$ to $R^5$ independently of one another are hydrogen, but at most 4, are hydrogen at the same time, or $C_1$–$C_8$-alkyl or cycloalkyl, and also $R^1/R^2$ and/or $R^3/R^4$ can form a carbocyclic ring having from 5 to 7 ring atoms.

According to the present invention, particular preference is given to benzylidene-γ-butyrolactones in which the lactone ring is trisubstituted at $R^1$, $R^3$ and $R^4$ by an alkyl, where an alkyl group includes at least one $C_2$ chain. Likewise preferred are benzylidene-γ-butyrolactones whose benzylidene ring is substituted in the para-position by a methoxy radical, and $R^1$ is an ethyl radical, $R^2$ is hydrogen, and $R^3/R^4$ is a methyl radical.

Specific benzylidene-γ-butyrolactones compounds of the present invention include: p-Methoxybenzylidene-4-methyl-γ-butyrolactone, p-methoxybenzylidene-4-butyl-γ-butyrolactone, p-methoxybenzylidene-4,4-dimethyl-γ-butyrolactone, p-methoxy-benzylidene-3,4-dimethyl-γ-butyrolactone, p-methoxybenzylidene-3,4,4-trimethyl-γ-butyrolactone, p-methoxybenzylidene-3-methyl-4-pentyl-γ-butyrolactone, p-methoxybenzyl-idene-3-methyl-4-hexyl-γ-butyrolactone, o,p-dimethoxybenzylidene-4-butyl-γ-butyrolactone, o,p-dimethoxybenzylidene-4,4-dimethyl-γ-butyrolactone, o,p-dimethoxybenzylidene-3,4-dimethyl-γ-butyrolactone, m,p-dimethoxybenzylidene-4-butyl-γ-butyrolactone, m,p-dimethoxybenzyl-idene-4,4-dimethyl-γ-butyrolactone, m,p-dimethoxybenzylidene-3,4-dimethyl-γ-butyrolactone, p-methoxybenzylidene-3-ethyl-4,4-dimethyl-γ-butyrolactone, p-methoxybenzylidene-3,4-dimethyl-4-butyl-γ-butyro-lactone, p-methoxybenzylidene-3,4-dimethyl-4-ethyl-γ-butyrolactone. Particularly preferred benzylidene-γ-butyrolactones include p-methoxybenzylidene-3-ethyl-4,4-dimethyl-γ-butyrolactone, p-methoxybenzylidene-3,4-dimethyl-4-butyl-γ-butyrolactone, p-methoxybenzylidene-3,4-dimethyl-4-ethyl-γ-butyrolactone.

The benzylidene-γ-butyrolactones according to the present invention can be prepared in accordance with the prior art by aldol condensation of substituted benzaldehydes, for example anisaldehyde, with correspondingly substituted γ-butyrolactones, for example β-ethyl-γ,γ-dimethyl-γ-butyrolactone.

Additionally, the benzylidene-γ-butyrolactones according to the present invention are particularly suitable as UV absorbers and solvents for solid UV absorbers, which have relatively poor solubility within a pharmaceutical or cosmetic preparation. Accordingly, the present invention also provides compositions which comprise the above-mentioned benzylidene-γ-butyrolactones and are suitable for protecting against harmful UV radiation. In this connection, the compositions according to the present invention can comprise one or more of the benzylidene-γ-butyrolactones according to the invention.

Preference is given to compositions which comprise from 0.1 to 15% by weight of benzylidene-γ-butyrolactones according to the present invention, based on the total weight of the preparation. Particular preference is given to compositions comprising from 1 to 10% by weight, and most preferably comprising from 2 to 7% by weight, of benzylidene-γbutyrolactone according to the present invention.

According to the present invention, the above-mentioned compositions are preferably suitable as sunscreens or daycare products for protecting human skin and hair, in particular hair already predamaged by permanent waving, coloring and bleaching, against harmful UV radiation.

According to the present invention, the compositions can also be mixed with additives known per se and/or known UV absorbers of other classes of substance and/or known pigments.

Examples of common additives are emulsifiers, surface-active compounds, lanolin, petroleum jelly, water, triglycerides of fatty acids, polyethylene glycols, fatty alcohols, ethoxylated fatty alcohols, fatty acid ester such as, for example, isopropyl palmitate, isooctyl sterate, diisopropyl adipate etc., natural or synthetic oils or waxes, thickeners, such as, for example, hydroxyethylcellulose, bentonite, etc., preservatives, moisturizers, vitamins, skin-lightening active ingredients such as, for example, hydroquinones, arbutin, kojic acid and derivatives, ascorbic acid and derivatives, glutathione, hydroxybenzaldoximes, e.g., 4-hydroxy-3-methoxybenzaldehyde oxime, antioxidants such as, for example, BHT, vitamin derivatives, catechol derivatives, e.g., epigallocatechol gallate or 3,4-dihydroxybenzaldehyde oxime, complexing agents such as, for example, EDTA and derivatives, insect repellents such as, for example, DEET or IR 3535, silicone oils, glycerol, ethyl alcohol and perfume oils. The list of additives is not limited to the examples given. Pigments which can be added are, for example, titanium dioxide, zinc oxide, pearlizing pigments or color pigments.

Examples of traditional UV absorbers include p-aminobenzoic acid, ethyl p-amino-benzoate (25 mol) ethoxylated, 2-ethylhexyl p-dimethyl-aminobenzoate, ethyl p-aminobenzoate (2 mol) N-propoxylated, glycerol p-aminobenzoate, homomenthyl salicylate, 2-ethylhexyl salicylate, triethanolamine salicylate, 4-isopropylbenzyl salicylate, methyl anthranilate, ethyl diisopropylcinnamate, 2-ethylhexyl p-methoxy-cinnamate, methyl diisopropylcinnamate, isoamyl p-methoxycinnamate, p-methoxy-cinnamic acid diethanolamine salt, isopropyl p-methoxycin-namate, 2-ethylhexyl 2-cyano-3,3-diphenyl acrylate, ethyl 2-cyano-3,3'-diphenyl acrylate, 2-phenyl-benzimidazolesulphonic acid and salts, 3-(4'-trimethylammonium)-benzylidene-bornan-2-one methylsulphate, terephthalylidene-dibornanesulphonic acid and salts, 4-t-butyl-4'-methoxydibenzoylmethane, β-imidazole-4(5)-acrylic acid (urocanic acid). 2-hydroxy-4-methoxybenzophenone, 2-hydroxy-4-methoxybenzophenone-5-sulphonic acid, dihydroxy-4-methoxybenzophenone, 2,4-dihydroxy-benzophenone, tetrahydroxybenzophenone, 2,2'-dihydroxy-4,4'-dimethoxybenzophenone, 2-hydroxy-4-n-octoxybenzophenone, 2-hydroxy-4-methoxy-4'-methylbenzophenone, 3-(4'sulpho)benzylidene-bornan-2-one and salts, 3-(4'-methylbenzylidene)-d,1camphor, 3-benzylidene-d,1-camphor, 4-isopropyldibenzoylmethane, 2,4,6trianilino-(p-carbo-2'-ethylhexyl-1'-oxy)-1,3,5-triazine, phenylene-bis-benzimidazyl-tetrasulphonic acid disodium salt and N-[(2 and 4)-[2-(oxoborn-3ylidene) methyl]benzyl]-acrylamide polymer, benzylidene malonate polymer, 2,2'-methylene-bis-(6-(2H-benzotriazol-2-yl)-4-(1,1,3,3-tetramethylbutyl)-phenol), 2,2'-(1,4-phenylene)bis-1H-benzimidazol-4,6-disulphonic acid, monosodium salt, 2,4-bis-((4-(2-ethyl-hexyloxy)-2-hydroxy)-phenyl)-6-(4-methoxyphenyl)-(1,3,5)-triazine.

UV absorbers which have proven to be particularly suitable for combination with the agents according to the present invention are 2-ethylhexyl p-methoxycinnamate, isoamyl p-methoxycinnamate, 2-phenylbenzimidazolesulphonic acid, 3-(4'-methylbenzylidene)-d,1-camphor, 2-ethylhexyl 2-cyano-3,3-diphenylacrylate, 2-ethylhexyl salicylate, 4-tert-butyl-4'-methoxydibenzoylmethane and phenylene-bis-benzimidazyl-tetrasulphonic acid disodium salt, indanylidene derivatives according to DE 19 631 863 and benzazol derivatives according to DE 19 648 010.

The present invention further provides for the use of the agents according to the present invention in combination with conventional UV absorbers for enhancing the protection against harmful UV radiation above the degree of protection which is achieved using equal amounts of conventional UV absorbers alone or the agents alone (synergistic effect).

Furthermore, the agents according to the present invention can also be combined with conventional UV absorbers which are used for the protection of industrial products, such as paints, surface coatings, plastics, textiles, packaging materials or rubber.

Examples of such UV absorbers are compounds from the group consisting of benzotriazoles, benzophenones, triazines, cinnamic esters and oxalanilides.

The compositions according to the present invention can be in the form of any currently customary cosmetic or pharmaceutical preparations. For example, they can be supplied as emulsion, milk, lotion, cream, gel, aerosol, shampoo, conditioner, intensive conditioner or spray.

Surprisingly, the compositions which comprise benzylidene-γ-butyrolactone in accordance with the present invention are characterized by a combination of desirable properties.

The agents have the advantageous properties according to the present invention in that they have high UV protection even at low use concentrations, excellent photo-stability and thermal stability and good solubility in cosmetic solvents. In addition, the crystalline, oil-soluble UV absorbers have, in accordance with the present invention, excellent solubility in cosmetic solvents. The agents have, in accordance with the invention, good compatibility with cosmetic bass and good pH stability, are colorless, neutral in odor and water-resistant. In addition, the agents according to the present invention can be incorporated without problems into cosmetic preparations and exhibit good stability under use conditions and good compatibility with packaging materials. Moreover, the compositions according to the present invention do not cause any discoloration of textiles and can be washed out easily.

The application is illustrated in more detail below by reference to the examples:

EXAMPLES

1. Benzylidene-γ-butyrolactones according to the present invention and their preparation By way of example for the preparation of the benzylidene-γ-butyrolactones according to the invention, the preparation of p-methoxybenzylidene-4-methyl-γ-butyrolactone as Example 1 may be illustrated in more detail.

Example 1
p-Methoxybenzylidene-4-methyl-γ-butyrolactone 74 g (0.5 mol) of 4-methyl-γ-butyrolactone are added to a suspension of 27 g (0.50 mol) of sodium methoxide in 400 g of methyl tert-butyl ether and, over the course of 1 h, 68 g (0.5 mol) of anisaldehyde are added thereto with stirring at room temperature. The mixture is maintained under reflux for a further 1 h and then cooled, and 200 g of iced water are added to the mixture and the pH is adjusted to 5 using 10% sulphuric acid. After the phases have separated, the product is distilled. This gives 65 g of the desired compound in a yield of 48% of theory. The specific absorbance $E^{1}\!/\!_{1}$ of the novel compound according to the present invention is 1.250, measured at a wavelength of $\lambda_{max}$ 310 nm.

Example 2
p-Methoxybenzylidene-4,4-dimethyl-γ-butyrolactone

Analogous process using 4,4-dimethyl-γ-butyrolactone. $E^{1}\!/\!_{1}$ 1.200 ($\lambda_{max}$ 310 nm).

Example 3
p-Methoxybenzylidene-3,4-dimethyl-γ-butyrolactone

Analogous process using 3,4-dimethyl-γ-butyrolactone. $E^{1}\!/\!_{1}$ 1.050 ($\lambda_{max}$ 314 nm).

Example 4
p-Methoxybenzylidene-3,4,4-trimethyl-γ-butyrolactone

Analogous process using 3,4,4-trimethyl-γ-butyrolactone. $E^{1}\!/\!_{1}$ 1.060 ($\lambda_{max}$ 312 nm).

Example 5
p-Methoxybenzylidene-3-ethyl-4,4-dimethyl-γ-butyrolactone

Analogous process using 3-ethyl-4,4-dimethyl-γ-butyrolactone. $E^{1}\!/\!_{1}$ 940 ($\lambda_{max}$ 312 nm).

Example 6
p-Methoxybenzylidene-3-methyl-4-pentyl-γ-butyrolactone

Analogous process using 3-methyl-4-pentyl-γ-butyrolactone. $E^{1}\!/\!_{1}$ 830 ($\lambda_{max}$ 313 nm).

Example 7
p-Methoxybenzylidene-3,4-dimethyl-4-butyl-γ-butyrolactone

Analogous process using 3,4-dimethyl-4-butyl-γ-butyrolactone. $E^{1}\!/\!_{1}$ 810 ($\lambda_{max}$ 312 nm).

Example 8
p-Methoxybenzylidene-3,4-dimethyl-4-ethyl-γ-butyrolactone

Analogous process using 3,4-dimethyl-4-ethyl-γ-butyrolactone. $E^{1}\!/\!_{1}$ 960 ($\lambda_{max}$ 311 nm).

2. Compositions according to the present invention, their preparation and determination of the sun protection factor:

The composition and the preparation procedure for various sunscreens according to the present invention are listed in Examples 9 to 14. In this connection, (O/W) indicates that it is an oil-in-water emulsion. The abbreviation (W/O) indicates a water-in-oil emulsion. Example 15 describes the composition and preparation of a sunscreen oil, Example 16 a sunscreen cream or a sunscreen gel, and Example 17 discloses the constituents and preparations of a hair shampoo according to the present invention.

Example 9
Sunscreen lotion (O/W)

PREPARATION PROCEDURE:

Part A: Melt at about 80° C.

Part B: Heat to about 90° C., add Part B to Part A with stirring.

Part C: Disperse Carbopol in water until lump-free, neutralize the sodium hydroxide solution to give a gel, add to Part A/B at about 60° C. Stir until the temperature drops to room temperature.

Part D: Perfume the emulsion at about 30° C., check the pH (6.5 to 7.0).

TABLE 1

| | CONSTITUENTS | % |
|---|---|---|
| A) | Arlatone 983 S | 1.75 |
| | Brij 76 | 1.25 |
| | Lanette O | 1.15 |
| | Myritol 318 | 15.00 |
| | Cetiol SN | 15.00 |
| | Phenonip | 0.20 |
| | UV absorber | 5.00 |
| | p-Methoxybenzyliden-3,4-dimethyl-4-ethyl-γ-butyrolactone 1–10% | |
| B) | Water, dist. | 31.65 |
| | 1,2-Propylene glycol | 2.00 |
| | Phenonip | 0.30 |
| C) | Water, dist. | 25.00 |
| | Carbopol 2984 | 0.30 |
| | Sodium hydroxide, 10% in water | 1.00 |
| D) | Perfume oil | 0.40 |

Example 10
Sunscreen milk (W/O)

PREPARATION PROCEDURE:

Part A: Thorough melt at about 90° C.

Part B: Heat to bout 95° C., then add Part B to Part A with stirring. Stir until the temperature drops to room temperature.

Part C: Ad Part C at 30° C. and then homogenize.

TABLE 2

| | CONSTITUENTS | % |
|---|---|---|
| A) | Dehymuls PG PH | 5.00 |
| | Permulgin 3220 | 0.50 |
| | Zinc stearate | 0.50 |
| | Myritol 318 | 15.00 |
| | Cetiol SN | 15.00 |
| | UV absorber | 5.00 |
| | p-Methoxybenzyliden-3,4-dimethyl-4-ethyl-γ-butyrolactone | |
| B) | Water, dist. | 52.50 |
| | Glycerol 86% | 5.00 |
| | Magnesium sulphate 7 $H_2O$ | 0.50 |
| | Phenonip | 0.50 |
| C) | Perfume oil | 0.50 |

Example 11
Sunscreen lotion (O/W)

PREPARATION PROCEDURE:

Part A: Melt at about 80° C.

Part B: Heat at about 90° C. Add Part B to Part A with stirring.

Part C: Disperse Carbopol in water until lump-free, neutralize with sodium hydroxide solution to give a gel, add to Part A/B at about 60° C. Stir until the temperature drops to room temperature.

Part D: Perfume the emulsion at about 30° C., check the pH (6.5 to 7.0).

TABLE 3

| | CONSTITUENTS | % |
|---|---|---|
| A) | Arlatone 983 S | 1.75 |
| | Brij 76 | 1.25 |
| | Lanette O | 1.15 |
| | Myritol 318 | 15.00 |
| | Cetiol SN | 15.00 |
| | Finsolv TN | 5.00 |
| | Phenonip | 0.20 |
| | UV absorber p-Methoxybenzyliden-3,4-dimethyl-4-ethyl-γ-butyrolactone | 4.00 |
| | Parsol 1789 | 1.50 |
| B) | Water, dist. | 26.15 |
| | 1,2-Propylene glycol | 2.00 |
| | Phenonip | 0.30 |
| C) | Water, dist. | 25.00 |
| | Carbopol 2984 | 0.30 |
| | Sodium hydroxide, 10% strength in water | 1.00 |
| D) | Perfume oil | 0.40 |

Example 12

Sunscreen lotion (O/W)

PREPARATION PROCEDURE:

Part A: Melt at about 80° C.

Part B: Heat at about 90° C. Add Part B to Part A with stirring.

Part C: Disperse Carbopol in water until lump-free, neutralize with sodium hydroxide solution to give a gel, add to Part A/B at about 60° C. Stir until the temperature drops to room temperature.

Part D: Perfume the emulsion at about 30° C., check the pH (6.5 to 7.0).

TABLE 4

| | CONSTITUENTS | % |
|---|---|---|
| A) | Arlatone 983 S | 1.75 |
| | Brij 76 | 1.25 |
| | Lanette O | 1.15 |
| | Myritol 318 | 12.00 |
| | Cetiol SN | 12.00 |
| | UV absorber p-Methoxybenzyliden-3,4-dimethyl-4-ethyl-γ-butyrolactone | 7.00 |
| | NEO HELIOPAN ® E 1000 | 7.00 |
| | Phenonip | 0.20 |
| B) | Water, dist. | 28.65 |
| | 1,2-Propylene glycol | 2.00 |
| | Phenonip | 0.30 |
| C) | Water, dist. | 25.00 |
| | Carbopol 2984 | 0.30 |
| | Sodium hydroxide, 10% strength in water | 1.00 |
| D) | Perfume oil | 0.40 |

Example 13

Sunscreen lotion (O/W)

PREPARATION PROCEDURE:

Part A: Melt at about 80° C., then thoroughly disperse Eusolex TA.

Part B: Heat at about 90° C. without Veegum and Natrosol, then disperse Veegum and Natrosol, add Part B to Part A with stirring. Stir until the temperature drops to room temperature.

Part C: Ad Part C at 30° C. and then homogenize. Check the pH (7.0–7.5).

TABLE 5

| | CONSTITUENTS | % |
|---|---|---|
| A) | Arlacel 165 | 3.00 |
| | Eumulgin B 2 | 1.00 |
| | Lanette | 1.00 |
| | Myritol 318 | 4.00 |
| | Cetiol OE | 2.00 |
| | Abil 100 | 1.00 |
| | Bentone Gel MIO | 3.00 |
| | Cutina CBS | 1.00 |
| | Phenonip | 0.20 |
| | NEO HELIOPAN ® OS (octyl salicylate) | 3.00 |
| | NEO HELIOPAN ® AV (octyl methoxycinnamate) | 5.00 |
| | NEO HELIOPAN ® E 1000 (isoamyl p-methoxycinnamate) | 5.00 |
| | NEO HELIOPAN ® MBC (4-methylbenzylidene camphor) | 1.00 |
| | Eusolex TA | 3.00 |
| | UV absorber p-Methoxybenzyliden-3,4-dimethyl-4-ethyl-γ-butyrolactone | 3.00 |
| B) | Water, dist. | 45.60 |
| | Glycerol, 86% strength | 3.00 |
| | Phenonip | 0.30 |
| | Veegum Ultra | 1.00 |
| | Natrosol 250 HHR | 0.30 |
| | NEO HELIOPAN ® HYDRO, used as a 15% strength solution after neutralization with sodium hydroxide (phenyl benzimidazole sulphonic acid) corresponds to active substance: 2.0% | 13.30 |
| C) | Perfume oil | 0.30 |

Example 14

Sunscreen lotion (O/W)

PREPARATION PROCEDURE:

Part A: Thoroughly melt at about 90° C. (without ZINKOXID NEUTRAL H&R). Then thoroughly disperse ZINKOXID NEUTRAL H&R.

Part B: Heat at about 95° C., then add Part B to Part A with stirring. Stir until the temperature drops to room temperature.

Part C: Add Part C at 30° C. and then homogenize.

TABLE 6

| | CONSTITUENTS | % |
|---|---|---|
| A) | Arlacel 1689 | 3.50 |
| | Finsolv TN | 6.00 |
| | NEO HELIOPAN ® E 1000 (isoamyl p-methoxycinnamate) | 7.00 |
| | Uvinul T 150 (octyl triazone) | 1.00 |
| | UV absorber p-Methoxybenzyliden-3,4-dimethyl-4-ethyl-γ-butyrolactone | 3.00 |
| | Copherol F 1250 | 2.00 |
| | Permulgin 2550 | 1.00 |
| | Myritol 318 | 6.00 |
| | Cetiol SN | 6.00 |
| | ZINKOXID NEUTRAL H&R (zinc oxide) | 7.00 |
| B) | Water, dist. | 51.70 |
| | Glycerol 86% strength | 5.00 |
| | Phenonip | 0.50 |
| C) | Perfume oil | 0.30 |

Example 15

Sunscreen oil

PREPARATION PROCEDURE:

Thoroughly mix and constituents.

TABLE 7

| | CONSTITUENTS | % |
|---|---|---|
| A) | NEO HELIOPAN ® E 1000 (isoamyl p-methoxycinnamate) | 7.50 |
| | NEO HELIOPAN ® OS (octyl salicylate) | 5.00 |
| | UV absorber p-Methoxybenzyliden-3,4-dimethyl-4-ethyl-γ-butyrolactone | 3.00 |
| | Myritol 318 | 34.70 |
| | Diisopropyl adipate | 5.00 |
| | Olive oil | 1.00 |
| | Jojoba oil | 1.00 |
| | Macadamia nut oil | 1.00 |
| | Tocopherol oil | 1.00 |
| | Isopropyl myristate | 35.00 |
| | Antaron V-216 | 5.00 |
| | Phenonip | 0.50 |
| | Perfume oil | 0.30 |

Example 16

Sunscreen cream gel

PREPARATION PROCEDURE:

Part A: dissolve ingredients in the water.

Part B: Mix all constituents (without Permulen and Carbopol). Dissolve NEO HELIOPAN® MBC and UV absorber according to formula (I) with gentle warming. Disperse Carbopol and Permulen. Then add Part B to Part A and mix vigorously for 45 minutes.

Part C: Add triethanolamine to Part A/B with stirring. Continue stirring until the product is homogeneous. Check the pH (about 7.0).

TABLE 8

| | CONSTITUENTS | % |
|---|---|---|
| A) | Water, dist. | 75.35 |
| | Phenonip | 0.50 |
| | EDTA B liquid | 0.10 |
| B) | NEO HELIOPAN ® AV (octyl methoxycinnamate) | 7.00 |
| | NEO HELIOPAN ® 303 (octocrylene) | 3.00 |
| | NEO HELIOPAN ® MBC (4-methylbenzylidene camphor) | 1.00 |
| | UV absorber p-Methoxybenzyliden-3,4-dimethyl-4-ethyl-γ-butyrolactone | 3.00 |
| | Cetiol SN | 5.00 |
| | Eutanol G | 3.00 |
| | Lameform TG 1 | 1.00 |
| | Perfume oil | 0.30 |
| | Permulen TR-1 | 0.25 |
| | Carbopol 954 | 0.05 |
| C) | Triethanolamine | 0.45 |

Example 17

Hair shampoo

Part A: Dissolve UV absorber in NEO HELIOPAN® E 1000 and Phenonip and with gentle warming, then add Arlatone G and perfume oil and mix well. Weigh in the remaining constituents.

Part B: Dissolve polymer in the water with stirring, and add and dissolve the remaining constituents. Add Part B to Part A and stir (check the pH, about 5.5).

TABLE 9

| | CONSTITUENTS | % |
|---|---|---|
| A) | Genapol LRO liquid | 18.00 |
| | Texapon MG3 | 36.00 |
| | Lamepon S | 6.00 |
| | Perfume oil | 0.60 |
| | Phenonip | 0.50 |
| | Arlatone G | 2.00 |
| | UV absorber p-Methoxybenzyliden-3,4-dimethyl-4-ethyl-γ-butyrolactone | 0.50 |
| B) | Water, dist. | 34.00 |
| | Polymer JR 400 | 0.20 |
| | D-Panthenol | 1.00 |
| | Sodium chloride | 1.00 |
| | Sodium hydroxide, 10% strength in water | 0.20 |

PREPARATION PROCEDURE:

3. Commercially available substances used to prepare the compositions according to the invention:

The commercially available substances used in Point 2 to prepare the compositions according to the invention, and their suppliers are summarized below:

TABLE 10

| Trade name | Chemical name | Supplier |
|---|---|---|
| Abil 100 | Polydimethylsiloxane | 7 |
| Antaron V-216 | Vinylpyrrolidone/hexadecene copolymer | 18 |
| Arlacel 1689 | Sorbitan monooleate/propylglyceryl-3-ricinoleate | 4 |
| Arlacel 165 | Glycerol stearate/polyethylene glycol (MW 100) stearate mixture | 4 |
| Arlatone G | hydrogenated with 25 mol of ethylene oxide | 4 |
| Arlatone 983 S | Polyethylene glycol (MW 5) glyceryl stearate | 4 |
| Baysilone Fluid PK 20 | Silicone oil | 5 |
| Betone Gel MIO | Mineral oil, quaternium-18 hectorite, propylene carbonate | 17 |
| Brij 76 | Polyethylene glycol (MW 10) stearyl ether | 4 |
| Carbopol 2984 | Polyacrylic acid | 2 |
| Carbopol 954 | Polyacrylic acid | 2 |
| Cetiol HE | Polyol fatty acid ester | 3 |
| Cetiol OE | Dicaprylyl ether | 3 |
| Cetiol SN | Cetyl/stearyl isononanoate | 3 |
| Copherol F 1250 | D-α-Tocopheryl acetate | 3 |
| Cutina CBS | Glycerol stearate, cetyl/stearyl alcohol cetyl palmitate, coconut glycerides | 3 |
| Dehymuls PG PH | Polyglycerol poly-12-hydroxystearate | 3 |
| Diisopropyl adipate | Diisopropyl adipate | 3 |
| D-Panthenol | Panthothenyl alcohol | 15 |
| EDTA B liq. | Tetrasodium ethylenediaminetetraacetic acid | 6 |
| Eusolex TA | Titanium dioxide | 13 |
| Eutanol G | 2-Octyldodecanol | 3 |
| Eumulgin B2 | Cetyl/stearyl alcohol, etherified with 20 mol of ethylene oxide | 3 |
| Finsolv TN | Alkyl benzoate | 23 |
| Genapol LRO liq. | Sodium lauryl sulphate | 9 |
| Glycerol | 1,2,3-Propanetriol | 3 |
| Isopropyl myristate | Isopropyl myristate | 3 |
| Jojoba oil | Jojoba oil | 19 |
| Lameform TGI | Triglycerol diisostearate | 3 |
| Lameform S | Protein/coconut fatty acid condensate. potassium salt | 3 |
| Lanette 0 | Cetyl/stearyl alcohol mixture | 3 |
| Macadamia nut oil | Macadamia nut oil | 20 |
| Myritol 318 | Capryl/capric triglyceride | 3 |
| Natrosol 250 HHR | Hydroxyethylcellulose | 11 |
| NEO HELTOPAN ®AV | Isooctyl p-methoxycinnamate | 1 |
| NEO HELIOPAN ®BB | 2-Hydroxy-4-methoxybenzophenone | 1 |
| NEO HELIOPAN ®E 1000 | Isoamyl p-methoxycinnamate | 1 |
| NEO HELIOPAN ®HYDRO | Phenylbenzimidazolesulphonic acid | 1 |
| NEO HELIOPAN ®BC | 3-(4-Methylbenzylidene)-d, 1-camphor | 1 |
| NEO HELIOPAN ®OS | 1-Ethylhexyl salicylate | 1 |
| NEO HELIOPAN ®303 | Isooctyl α-phenyl-β-cyanocinnamate | 1 |
| Olive oil | Olive oil | 21 |
| Parsol 1789 | Butylmethoxydibenzoylmethane | 12 |
| Permulgin 2550 | Wax | 14 |
| Permulgin 3220 | Wax | 14 |
| Permulen TR 1 | Polyacrylate | 2 |
| Phenonip | Mixture of p-hydroxybenzoic esters and phenoxyethanol | 8 |
| Polymer JR 400 | Polyquaternium-10 | 21 |
| 1,2-Propylene glycol | 1,2-Propanediol | 6 |
| Texapon MG 3 | Magnesium lauryl sulphate/disodium lauryl sulphosuccinate | 3 |
| Tocopherol oil | Soya oil with D-α-tocopherol | 22 |
| Uvinul T 150 | Isooctyl triazinyl-p-aminobenzoate | 6 |
| Veegum Ultra | Magnesium aluminium silicate | 10 |
| ZINC OXIDE NEUTRAL H&R | Zinc oxide | 1 |
| Zinc stearate | Zinc stearate | 16 |

Suppliers

TABLE 11

1. Haarmann & Reimer GmbH, Holzminden
2. B. F. Goodrich Company, Neuss
3. Henkel KGaA, Düsseldorf
4. ICI Speciality Chemicals, Frankfurt
5. Bayer AG, Leverkusen

TABLE 11-continued

6. BASF, Ludwigshafen
7. Goldschmidt AG, Essen
8. Nipa Lab, Ltd., Pontypridd Mid Glam., Wales/GB
9. Hoechst AG, Frankfurt
10. R. T. Vanderbilt Company Inc., Norwalk/USA
11. Hercules Inc., Wilmington, Delaware/USA

TABLE 11-continued

12. Hoffmann-LaRoche, Basle/CH
13. E. Merck, Darmstadt
14. Koster Keunen Holland BV, Bladl/NL
15. Akzo Chemie GmbH, Düren
16. Chemische Werke Bärlocher, Munich
17. Rheox Inc., Hightstown, New Jersey/USA
18. ISP Global Technologies Deutschland GmbH, Frechen
19. Henry Lamotte, Bremen
20. Erhard Wagner GmbH, Bremen
21. Nordmann & Rassmann GmbH & Co., Hamburg
22. Richter GmbH, Berlin
23. Witco Surfactants GmbH, Steinau a.d. Straße Although the invention has been described in detail in the foregoing for the purpose of illustration, it is to be understood that such detail is solely for that purpose and that variations can be made therein by those skilled in the art without departing from the spirit and scope of the invention except as it may be limited by the claims.

What is claimed is:

1. A benzylidene-γ-butyrolactone comprising the general formula

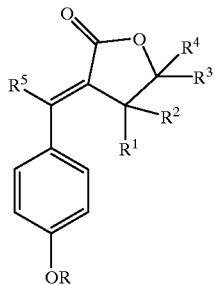

wherein

R is hydrogen or $C_1$–$C_6$-alkyl or cycloalkyl, and $R^1$ to $R^5$ independently of one another are hydrogen, but at most 4 are hydrogen at the same time, or $C_1$–$C_8$-alkyl or cycloalkyl, and also $R^1/R^2$ and/or $R^3/R^4$ form a carbocyclic ring having from 5 to 7 ring atoms, wherein $R^1$ to $R^5$ includes at least one $C_2$ chain.

2. A benzylidene-γ-butyrolactone according to claim 1, wherein the lactone ring is trisubstituted ($R^1$, $R^3$ and $R^4$=alkyl), wherein an alkyl group includes at least one $C_2$ chain.

3. A benzylidene-γ-butyrolactone according to either of claim 1, wherein the benzylidene ring is substituted in the para-position by a methoxy radical, and $R^1$ is ethyl, $R^2$ is hydrogen and $R^3/R^4$ is methyl.

4. A composition comprising at least one benzylidene-γ-butyrolactone having the general formula

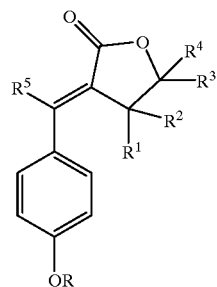

wherein

R is hydrogen or $C_1$–$C_6$-alkyl or cycloalkyl, and $R^1$ to $R^5$ independently of one another are hydrogen, but at most 4 are hydrogen at the same time, or $C_1$–$C_8$-alkyl or cycloalkyl, and also $R^1/R^2$ and/or $R^3/R^4$ form a carbocyclic ring having from 5 to 7 ring atoms, wherein $R^1$ to $R^5$ includes at least one $C_2$ chain.

5. A composition according to claim 4, wherein said composition comprises from 0.1 to 15% by weight of benzylidene-γ-butyrolactone, based on the total weight of the preparation.

6. A composition according to claim 5, wherein said composition comprises from 1 to 10% by weight of benzylidene-γ-butyrolactone, based on the total weight of the preparation.

7. A composition according to claim 6, wherein said composition comprises from 2 to 7% by weight of benzylidene-γ-butyrolactone, based on the total weight of the preparation.

8. A composition according to claim 4, wherein said benzylidene-γ-butyrolactone is a UV absorber and also a solvent.

9. A composition according to claim 4, wherein said composition comprises additives and optionally, UV absorbers and optionally, pigments.

10. A composition according to claim 4, wherein said composition is an emulsion, milk, lotion, cream, gel, aerosol, shampoo, conditioner, intensive conditioner, spray or any other customary cosmetic or pharmaceutical preparation.

11. A composition according to claim 4, wherein said benzylidene-γ-butyrolactone has high UV protection even at low use concentrations.

12. A composition according to claim 4, wherein said benzylidene-γ-butyrolactone has excellent photostability and thermal stability.

13. A composition according to claim 4, wherein said benzylidene-γ-butyrolactone has good solubility in cosmetic solvents.

14. A composition according to claim 4, wherein said benzylidene-γ-butyrolactone are crystalline, oil-soluble UV absorbers and have excellent solubility.

15. A composition according to claim 4, wherein said benzylidene-γ-butyrolactone shows good pH stability.

16. A composition according to claim 4, wherein benzylidene-γ-butyrolactone is colorless, neutral in odor and water-resistant.

17. A process for the preparation of compositions comprising the mixing of at least one benzylidene-γ-butyrolactone having the general formula

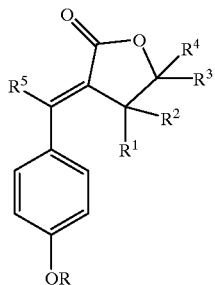

wherein

R is hydrogen or $C_1$–$C_6$-alkyl or cycloalkyl, and $R^1$ to $R^5$ independently of one another are hydrogen, but at most 4 are hydrogen at the same time, or $C_1$–$C_8$-alkyl or cycloalkyl, and also $R^1/R^2$ and/or $R^3/R^4$ form a carbocyclic ring having from 5 to 7 ring atoms, wherein $R^1$ to $R^5$ includes at least one $C_2$ chain;

with additives and optionally, UV absorbers and optionally, pigments.

18. A sunscreen or daycare product for protecting human skin and hair against harmful UV radiation comprising at least one benzylidene-γ-butyrolactone having the general formula

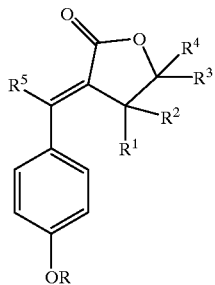

wherein

R is hydrogen or $C_1$–$C_6$-alkyl or cycloalkyl, and $R^1$ to $R^5$ independently of one another are hydrogen, but at most 4 are hydrogen at the same time, or $C_1$–$C_8$-alkyl or cycloalkyl, and also $R^1/R^2$ and/or $R^3/R^4$ form a carbocyclic ring having from 5 to 7 ring atoms, wherein $R^1$ to $R^5$ includes at least one $C_2$ chain.

19. An industrial product comprising at least one benzylidene-γ-butyrolactone having the general formula

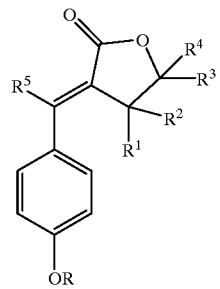

wherein

R is hydrogen or $C_1$–$C_6$-alkyl or cycloalkyl, and $R^1$ to $R^5$ independently of one another are hydrogen, but at most 4 are hydrogen at the same time, or $C_1$–$C_8$-alkyl or cycloalkyl, and also $R^1/R^2$ and/or $R^3/R^4$ form a carbocyclic ring having from 5 to 7 ring atoms, wherein $R^1$ to $R^5$ includes at least one $C_2$ chain.

20. A solvent for solid UV absorbers which have poor solubility within a cosmetic preparation comprising at least one benzylidene-γ-butyrolactone having the general formula

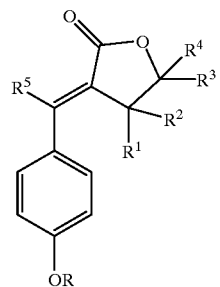

wherein

R is hydrogen or $C_1$–$C_6$-alkyl or cycloalkyl, and $R^1$ to $R^5$ independently of one another are hydrogen, but at most 4 are hydrogen at the same time, or $C_1$–$C_8$-alkyl or cycloalkyl, and also $R^1/R^2$ and/or $R^3/R^4$ form a carbocyclic ring having from 5 to 7 ring atoms, wherein $R^1$ to $R^5$ includes at least one $C_2$ chain.

21. A benzylidene-γ-butyrolactone according to claim 1, wherein said benzylidene-γ-butyrolactone is selected from the group consisting of p-methoxy-benzylidene-3-ethyl-4,4-dimethyl-γ-butyrolactone, p-methoxybenzylidene-3,4-dimethyl-4-butyl-γ-butyrolactone, or p-methoxybenzylidene-3,4-dimethyl-4-ethyl-γ-butyrolactone.

* * * * *